United States Patent [19]

Lindahl et al.

[11] Patent Number: 5,210,183

[45] Date of Patent: May 11, 1993

[54] PROTEIN ARP, WITH IMMUNOGLOBULIN A BINDING ACTIVITY, THE CORRESPONDING VECTORS AND HOSTS, REAGENT KIT AND PHARMACEUTICAL COMPOSITION

[75] Inventors: Gunnar Lindahl; Elisabet Frithz, both of Lund; Lars-Olof Heden, Dalby, all of Sweden

[73] Assignee: HighTech Receptor AB, Malmo, Sweden

[21] Appl. No.: 270,099

[22] Filed: Nov. 14, 1988

Related U.S. Application Data

[63] Continuation-in-part of Ser. No. 186,097, Apr. 25, 1988, abandoned.

[30] Foreign Application Priority Data

May 13, 1987 [EP] European Pat. Off. ......... 878501600

[51] Int. Cl.[5] .................... C07K 13/00; A61K 37/02; G01N 33/566
[52] U.S. Cl. ................................. 530/350; 436/513
[58] Field of Search .................. 530/350; 436/513; 514/2

[56] References Cited

PUBLICATIONS

Christensen et al., "A Reaction Between Some Streptococci and IgA Myeloma Proteins", Acta. Path. Microbiol. Scand. 83: 184-8 (1975).
Palmer et al. Lancet Jan. 7, 1989.
Schalen et al. Acta Path Microbiol Scand Sect C. 88:77-82 (1980).

Primary Examiner—David L. Lacey
Assistant Examiner—Shelly J. Guest
Attorney, Agent, or Firm—Cushman, Darby & Cushman

[57] ABSTRACT

This invention relates to a new protein subfragments thereof with affinity for immunoglobulin A, a process for cloning and expression of the protein, the corresponding vectors and hosts, a process for preparing the organism, a method for preparing the protein, a reagent kit and a pharmaceutical composition comprising the protein or fragments thereof.

6 Claims, 7 Drawing Sheets

FIG. IA

POSSIBLE PROMOTOR REGIONS AND THE RIBOSOME BINDING SITE (R.B.S.) ARE UNDERLINED. THE START OF THE MATURE PROTEIN IS INDICATED WITH AN ARROW.

```
1   CCTGGTCTTTACCTTTTACCGCTCATTCTTTAGAATAGAATTATTAGAGAGAAGTCTTAG
           ---35---                                    ---10---

61  AAAAATGAGGCTAATTCCCTAAAGATGAAAAAAATAAGGAGCAAATAATGGCTAGAAAA
                                     ---R.B.S.---      MetAlaArgLys

121 GATACGAATAAACAGTATTCGCTTAGAAAAAACAGGTACACAGCATCAGTAGCCGGTC
    AspThrAsnLysGlnTyrSerLeuArgLysThrGlyThrAlaSerValAlaVal
                                                         →
181 GCTGTGGCTGTGTTTAGGAGCAGGCTTTGCAAACCAAACAGAAGTTAAGGCTGCGGAGATT
    AlaValAlaValLeuGlyAlaGlyPheAlaAsnGlnThrGluValLysAlaAlaGluIle

241 AAAAAGCCTCAGGCTGATTCAGCGTGGAACTGGCCTAAAGAATATAACGCGTTACTTAAG
    LysLysProGlnAlaAspSerAlaTrpAsnTrpProLysGluTyrAsnAlaLeuLeuLys

301 GAAAATGAGGAGCTCAAGGTAGAACGTGAAAAAATATCTTATGCTGACGATAAAGAA
    GluAsnGluGluLeuLysValGluArgGluLysTyrAlaAspAspLysGlu
```

FIG. IB

```
361  AAAGATCCTCAATATAGAGCATTAATGGGTGAAAAATCAAGATCTTCGAAAAAGAGAGGGA
     LysAspProGlnTyrArgAlaLeuMetGlyGluAsnGlnAspLeuArgLysArgGluGly

421  CAATATCAGGACAAAATAGAAGAACTTGAAAAGAAAGAAAAACAAGAAAAGACAA
     GlnTyrGlnAspLysIleGluGluLeuGluLysGlnLysGluArgGlnLeuArgGln

481  GAACAATTAGAACGTCAATATCAAATAGAAGCAGATAAGCATTATCAAGAACAACAAAAG
     GluGlnLeuGluArgGlnTyrGlnIleGluAlaAspLysHisTyrGlnGluGlnGlnLys

541  AAACATCAGCAAGAACAACAATTAGAAGCAGAAAAACAAAAATTAGCTAAAGACAAA
     LysHisGlnGlnGluGlnGlnLeuGluGluLysGlnLysLeuAlaLysAspLys

601  CAAATCTCAGACGCAAGCCGTCAAGGCCTAAGCCGTGACCCTTGAAGCCGTCTCCGTGCAGCT
     GlnIleSerAspAlaSerArgGlnGlyLeuSerArgAspLeuGluAlaSerArgAlaAla

661  AAAAAGAGCTTGAAGCTGAGCACCAAAAACAAAGAGGAAAAACAAATCTCAGACGCA
     LysLysGluLeuGluLeuAlaGluHisGlnLysGluGluLysLeuLysGlnIleSerAspAla
```

FIG. IC

```
721  AGCCGTCAAGGTCTAAGCCGTGACCCTTGAAGGCCGTCTCGCGAAGCTTAAGAAAAAAGTAGAA
     SerArgGlnGlyLeuSerArgAspLeuGluAlaSerArgGluAlaLysLysValGlu

781  GCAGACCTAGCTGCTCTTACTGCTGAGCACCAAAAACTCAAAGAGGACAAACAAATCTCA
     AlaAspLeuAlaAlaLeuThrAlaGluHisGlnLysLeuLysGluAspLysGlnIleSer

841  GACGCAAGCCGTCAAGGCCTAAGCCGTGACCTTGAAGGCGTCTCGCGAACGTAAGAAAAAA
     AspAlaSerArgGlnGlyLeuSerArgAspLeuGluAlaSerArgGluArgLysLysLys

901  GTAGAAGCAGACTTAGCAGAAGCAAAATAGCAAACTTCAAGCCCTTGAAAAATTAGAAAAACAAA
     ValGluAlaAspLeuAlaAsnSerLysLeuGlnAlaLeuGluLysLeuAsnLys

961  GAGCTTGAAGAAGGTAAGAAGAAATTATCAGAAAAAGAAAAAGCTGAGTTACAAGCAAGACTA  1020
     GluLeuGluGluGlyLysLysLeuSerGluLysGluLysAlaGluLeuGlnAlaArgLeu

1021 GAAGCTGAAGCAAAAGCTCTTAAAGAGCAATTGGCTAAACAAGGGAAGAACTTGCTAAA    1080
     GluAlaGluAlaLysAlaLeuLysGluGlnLeuAlaLysGlnGlyLysAsnLeuAlaLys
```

FIG. 1D

```
1081  CTAAAAGGCAACCAACCACCAAAACGCTAAAGTAGCCCCACAAGTAGCTAACCGTTCTAGATCA  1140
      LeuLysGlyAsnGlnThrProAsnAlaLysValAlaProGlnAlaAsnArgSerArgSer

1141  GCAATGACACAACAAAAGAGAACGTTACCGTCAACAGGCGAAAAAGCTAACCCATTCTTT    1200
      AlaMetThrGlnGlnLysArgThrLeuProSerThrGlyGluLysAlaAsnProPhePhe

1201  ACAGCAGCAGCTGCAACAGTGATGATCTGCAGGTATGCTTCTAAAACTCAAAAGAA       1260
      ThrAlaAlaAlaAlaThrValMetValSerAlaGlyMetLeuAlaLeuLysLeuLysGlu

1261  GAAAACTAAGCTATTAGACTGATGCTAAGGAGAATCAAATGATTGTGTGTTTT          1320
      GluAsn

1321  GAGTGGCTAAGTAACTAACAATCTCAGTTAGACCAAAAAATGGGAATGGTTCAAAATGCT   1380

1381  GGCCTTTACTCCTTTTGATTAACCATATATAACAAAAACATTAGGAAAATAATAGTAATA   1440
```

FIG. IE

```
1441 TTAAGTTTATTTCCTCAATAAAATCAAGGAGTAGATAACGGCTAGACAACAAACCAAGAA 1500
1501 AAATTATTCACTACGGAAACTAAAAAACCGGTACGCTTCAGATGCGTTGCTTTTAGCCGTTT 1560
1561 TGGGTGCAGGTTTTCAAACCAAACAGAACTAAGAGCTGAAGGGGTAAAAGCGACTACGAA 1620
1621 CTTGCCAGAGAAGGCTAAATATGATGCATTGAGAGACGAGAATACTGGTTTACGTGGTGA 1680
1681 TCGGACAAAATTATTAAAAAACTTGAAGAAGAACAAGAGAAGAGCATAAAAAATCTAGAG 1740
1741 CATAAAAAACAGGAGTTAGAAAACCAAGCCCCTTAACTTTCATGATGTAATTGAAACTCAGG 1800
1801 AAAAGAAAAAGAAGATCTCAAAACAACTTTAGCTAAGACTACTAAAGAAAAATGAGATTT 1860
1861 CAGAAGCTAGTCGTAAAGGTCTAACA 1886
```

PROTEIN ARP, WITH IMMUNOGLOBULIN A BINDING ACTIVITY, THE CORRESPONDING VECTORS AND HOSTS, REAGENT KIT AND PHARMACEUTICAL COMPOSITION

This is a continuation-in-part of application Ser. No. 07/186,097, filed Apr. 25, 1988, now abandoned.

This invention relates to a new protein called Arp 4, variants and subfragments thereof with affinity for immunogobulin A, a process for cloning and expression of the protein, the corresponding vectors and hosts, a process for preparing the organism, a method for preparing the protein a reagent kit and a pharmaceutical composition comprising the protein or fragments thereof.

Bacterial surface proteins with affinity for immunoglobulins are important tools in modern immunology. The best known example of such a protein is protein A from *Staphylococcus aureus*, which is commonly used for the detection and isolation of IgG.

Bacterial proteins with affinity for other Ig classes than IgG would also be of considerable value as immunological tools. With regard to IgA, it is known that certain streptococcal strains bind IgA (Christensen and Oxelius, *Acta Path Microbiol Scand, Sect C*, 83, 184 (1975)), and isolation of an IgA-binding protein from group B streptococci has even been reported (Russell-Jones et al, *J Exp Med* 160, 1467 (1984)). However, the extraction method used by these authors—boiling of bacteria in 2% SDS—is not satisfactory for isolation of sufficient amounts of the protein, and the harshness of the procedure is likely to damage the protein. The protein is reported to have a molecular weight of 130 kDa.

In the aforesaid parent U.S. patent application of one of us, Lindahl, Ser. No. 07/186,097, filed Apr. 25, 1988, the entire disclosure of which is hereby incorporated herein by reference, there is described an IgA-binding protein, now called Arp 60, isolated from Streptococcus pyogenes strain AW 43. The present application concerns a similar protein with similar binding characteristics but with different N-terminal sequence. The gene for this new protein has been sequenced.

The present invention relates to a new protein, called Arp 4, which specifically binds to Immunoglobulin A and which has the amino acid sequence according to claim 1 and variants, subfragments or allelic derivates thereof, which specifically hinds to Immunoglobulin A.

The variants of the protein may be proteins which are deficient in one or more amino acids or in which one or more amino acids are replaced.

The new protein is an IgA receptor from group A streptococci with an apparent molecular weight of about 45 kDa on SDS-PAGE and with a N-terminal sequence starting at the arrow in FIG. 1 and going onwards to the right of the arrow.

The deduced amino acid sequence corresponds to a protein of 44 kDa with a 41 amino acids signal sequence and has the following amino acid composition including the signal sequence

| Residue | Number | Mole percent |
|---|---|---|
| Molecular weight = 43906.02 | | |
| Residue = 386 | | |
| A = Ala | 54 | 13.990 |
| C = Cys | 0 | 0.000 |
| D = Asp | 18 | 4.663 |
| E = Glu | 54 | 33.990 |

-continued

| Residue | Number | Mole percent |
|---|---|---|
| Molecular weight = 43906.02 | | |
| Residue = 386 | | |
| F = Pha | 3 | 0.777 |
| G = Gly | 12 | 3.109 |
| H = His | 4 | 1.036 |
| I = Ile | 6 | 1.554 |
| K = Lys | 56 | 14.508 |
| L = Leu | 40 | 10.363 |
| M = Mat | 5 | 1.295 |
| N = Asn | 13 | 3.368 |
| P = Pro | 7 | 1.813 |
| Q = Gln | 37 | 9.585 |
| R = Arg | 23 | 5.959 |
| S = Sar | 22 | 5.699 |
| T = Thr | 11 | 2.850 |
| V = Val | 11 | 2.850 |
| W = Tyr | 2 | 0.518 |
| Y = Tyr | 8 | 2.073 |

This new receptor, called protein Arp 4, binds to IgA but not to IgM, IgD or IgE. There is a weak binding of IgG, but this binding of IgG takes place at a separate site on the protein Arp molecule and does not interfere with the binding of IgA. The gene for protein Arp has been cloned into *Escherichia coli*, where it is expressed. This allows purification of the protein with gentle procedures.

The invention also concerns a gene according to claim 1.

The invention further claims a recombinant DNA molecule comprising a vector in which a DNA-sequence coding for a protein expressible in a microorganism has been inserted. characterized in that the DNA-sequence encodes for protein Arp and/or a fragment of this protein with substantially the same binding properties to immunoglobulin A.

The protein has been isolated from *Streptococcus pyogenes* strain AP4, and the corresponding DNA-sequence has been determined.

The invention further concerns a vector coding for the protein Arp 4 or fragments thereof, where the vector is chosen from plasmidsm, phage DNA or derivates or fragments thereof or combinations of plasmids and phage DNA and yeast plasmids, such as phage lambda (specifically phage lambda APR4 IgA # 6 Apr4 # 6 DSM 4931 at Deutsche Sammlung von Mikroorganismen (DSM).

Examples of vectors which can be used for cloning of DNA-sequences coding for protein Apr 4 and fragments thereof are bacterial plasmids such as plasmids from *E. coli*, phage DNA, e.g. phage lambda fragments or derivates thereof, such as phage lambda EMBL 3, vectors which are combinations of plasmids and phage DNA, yeast plasmids. The choice of the vector is done according to the microorganism used, i.e. the host.

The invention also concerns a host infected, transformed or trasfected with a recombinant DNA molecule comprising a vector in which a DNA-sequence coding for a protein expressible in a microorganism has been inserted. The inserted DNA is characterized in that the DNA-sequence codes for the protein Apr 4 and/or a fragment of this protein with substantially the same binding properties to immunoglobulin A. Suitable hosts that can be infected, transformed or transfected with a recombinant DNA molecule according to the invention and thereby express protein Arp 4 or fragments thereof are gram positive or negative bacteria such as *E. coli*, *Bacillus subtilis* and yeast cells. All sorts of *E. coli* strains can be used, preferably *E. coli* LE 392.

The invention also concerns a process for preparing an infected, transformed or transfected host defined above. Specifically, the invention concerns a process for infecting *E. coli* with phase lambda carrying the gene for protein Arp (preferably *E. coli* LE 392 transfected with phage lambda AP 4 IgA # 6).

The invention further concerns a process for preparing protein Arp and subfragments thereof with IgA binding activity, characterized in that an infected, transformed or transfected host defined above is cultivated and the protein isolated.

Preferably *E. coli* is infected with phage lambda containing the protein Arp 4 coding DNA-sequence and after lysis, the lysate liquid is separated from debris and purified by affinity chromatography with a ligand that has affinity for protein Arp 4. The ligand is preferably IgA (serum IgA, secretory IgA, $IgA_1$ or $IgA_2$). *E. coli* can be any strain, preferably LE 392, and it is grown in broth, preferably in LB broth. Preferably protease inhibitors such as iodoacetic acid and benzamidinechloride are added before the liquid lysate is separated.

The DNA-sequence that codes for protein Arp 4 or IgA-binding fragments thereof can be isolated from *S. pyogenes* strain AP4. The streptococcus cell wall is preferably made fragile and lyzed with enzymes, after which the DNA is purified by phenol extraction and density gradient centrifugation.

The streptococcus strains are cultivated in a rich medium, preferably in Todd-Hewitt both (oxoid). The cell wall can be made fragile by adding cysteine, threonine and glycine to the culture. The bacteria are lyzed by the addition of enzymes attacking the peptidoglycan layer (preferably mutanolysin), followed by sodium docecyl sulphate (SDS). The DNA is purified by phenol extraction and density gradient centrifugation.

The streptococcal DNA is treated with a restriction enzyme to yield fragments that can be ligated to the vector. The vector with inserted streptococcal DNA is then used to infect, transform or transfect a host cell. Production of protein Arp 4 is tested. When bacteriophage lambda is the vector, thus can be done by covering plates with plaques with a nitrocellulose membrane, which is then exposed to radioactive IgA or to IgA followed by peroxidase conjugated anti IgA. Positive reacting clones are collected.

Preferably the streptococcal DNA is treated with Sau 3AI to yield fragments in the size range of 10–20 kB. This DNA is ligated with T4 DNA ligase to lambda EMBL 3 arms which is allowed to infect *E. coli* P2392 which only allows phages with inserts to form plaques. The plates with plaques are covered with nitrocellulose membranes and analyzed as above, where presence of peroxidase is detected by staining with 3-amino-9-ethyl-carbazol.

Phage clones giving a positive signal contain the protein Arp 4 coding DNA, which can be cut out with restriction enzymes.

Preferably the DNA-sequence containing the protein Arp 4 gene is isolated by treating DNA from phage lambda E4 (AP4 IgA #6) with Sal I, followed by agarose gel electrophoresis and collection of the insert, with size 15.0 kB.

The DNA-sequence that codes for a protein or a peptide with IgA-binding activity could be any fragment of this insert or any similar nucleotide sequence that codes or and expresses such a protein or peptide or fragments thereof.

The protein or subfragments thereof can be used as a reagent for binding, separation and identification of immunogobulin A. Since IgA is the predominant antibody in mucous secretions, IgA-binding proteins are of considerable potential interest of the analysis of this important line of host defense.

The invention therefore also concerns a reagent kit containing protein Arp or subfragments thereof.

The new protein can also be used for absorption of immunoglobulin A from various biological specimens, such as the blood of patients with autoimmune disease.

Thus the invention also concerns a pharmaceutical composition containing protein Arp 4 or subfragments thereof as active ingredients possibly together with pharmaceutically acceptable adjuvants and excipients.

The protein according to the invention can be produced in *E. coli*, using the cloned gene. In our hands, cloning has been achieved by using bacteriophage lambda as the vector, but since our results show the the protein can indeed be produced in *E.coli*, it should also be possible to use other vectors than lambda and probably also other hosts than *E. coli*.

The invention is further described with the accompanying drawings of which

Binding of IgA to group A streptococci

Initial experiments were directed at finding a strain of group A streptococci with high capacity to bind IgA. Therefore a great number of streptococci group A were studied. Thus was done in binding assays with whole bacteria.

The group A streptococcal strains originate from two different collections. One series of 52 strains (the AP series) was originally received from Dr J Rotta in Prague; these strains all belong to different M types. A second series of 52 strains (the AW series) were obtained from Dr G Kronvall in Stockholm. The strains were grown in Todd-Hewitt both (Oxoid).

The binding test was performed as follows: The protein under study was labelled with carrier-free $^{125}I$ (Amersham International, England), using the chloramine T method (Greenwood F C, Hunter, W H and Glover, J S, *Biochem J* 89 114 (1963)). Free unreacted isotyope was separated from protein by egel chromatography on 9 ml columns of Sephadex G-25 (PD-10, Parmacia, Uppsala, Sweden). The specific activity of the radiolabelled immunoglobulins was 1–3 mCi/mg.

Duplicate samples containing 2-5 ng (about $10^4$ cpm) of radiolabelled immunoglobulin in 25 µl PBSAT (0.12M NaCl, 0.03M phosphate, 0.02% NaN$_3$, 0.05% Tween 20, pH 7.2) were mixed with $2 \times 10^8$ bacteria suspended in 200 µl PBSAT. Radiolabelling was performed with carrier-free $^{125}$I.

All assays were carried out in plastic tubes at room temperature.

Figure 1A:
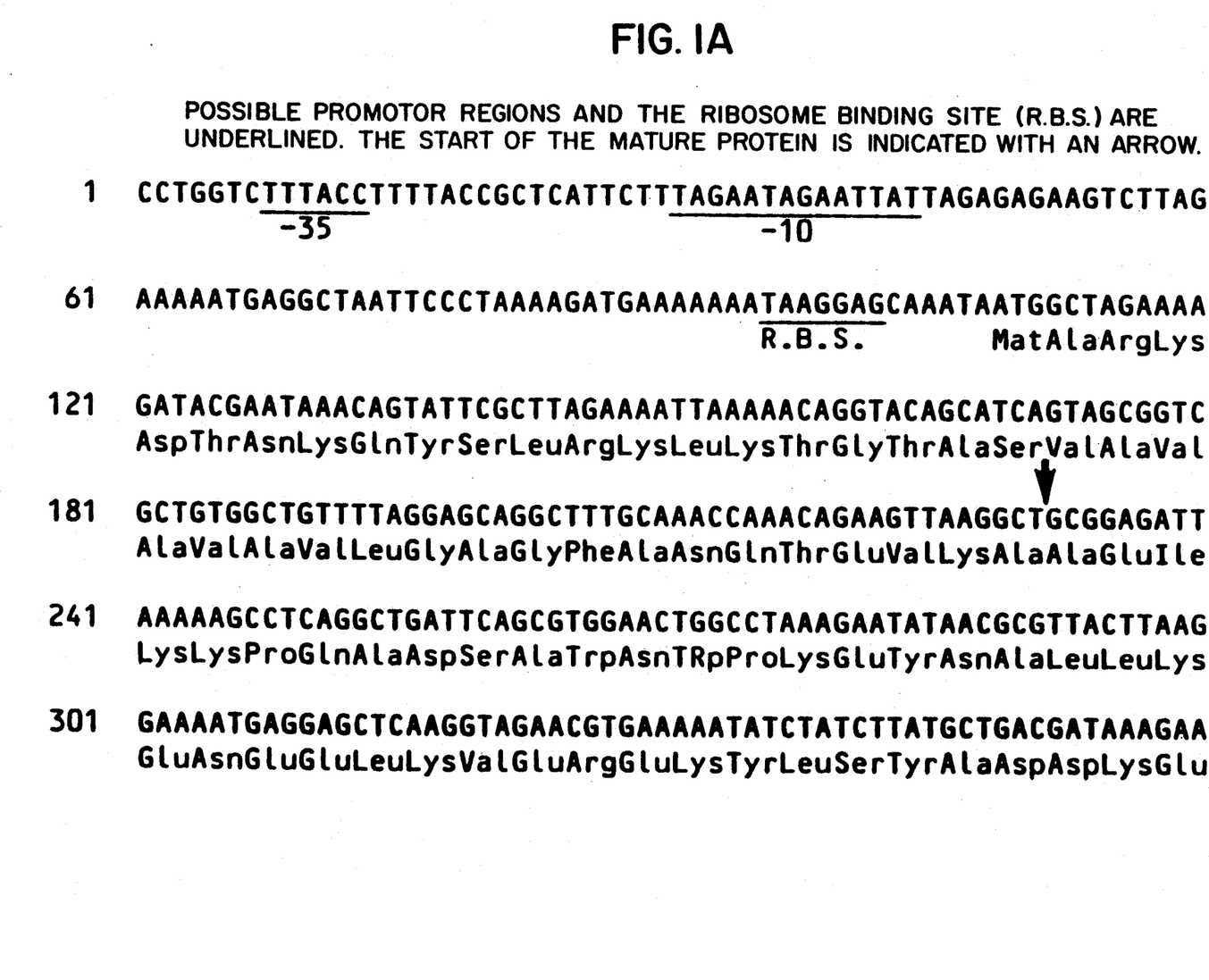
FIGS. 1A–1E shows the nucleotide sequence for the gene coding protein Arp 4 and the amino acid sequence. Possible promoter regions and the ribosome binding site (R.B.S.) are underlined. The start of the mature protein is indicated with an arrow.
Figure 1B:
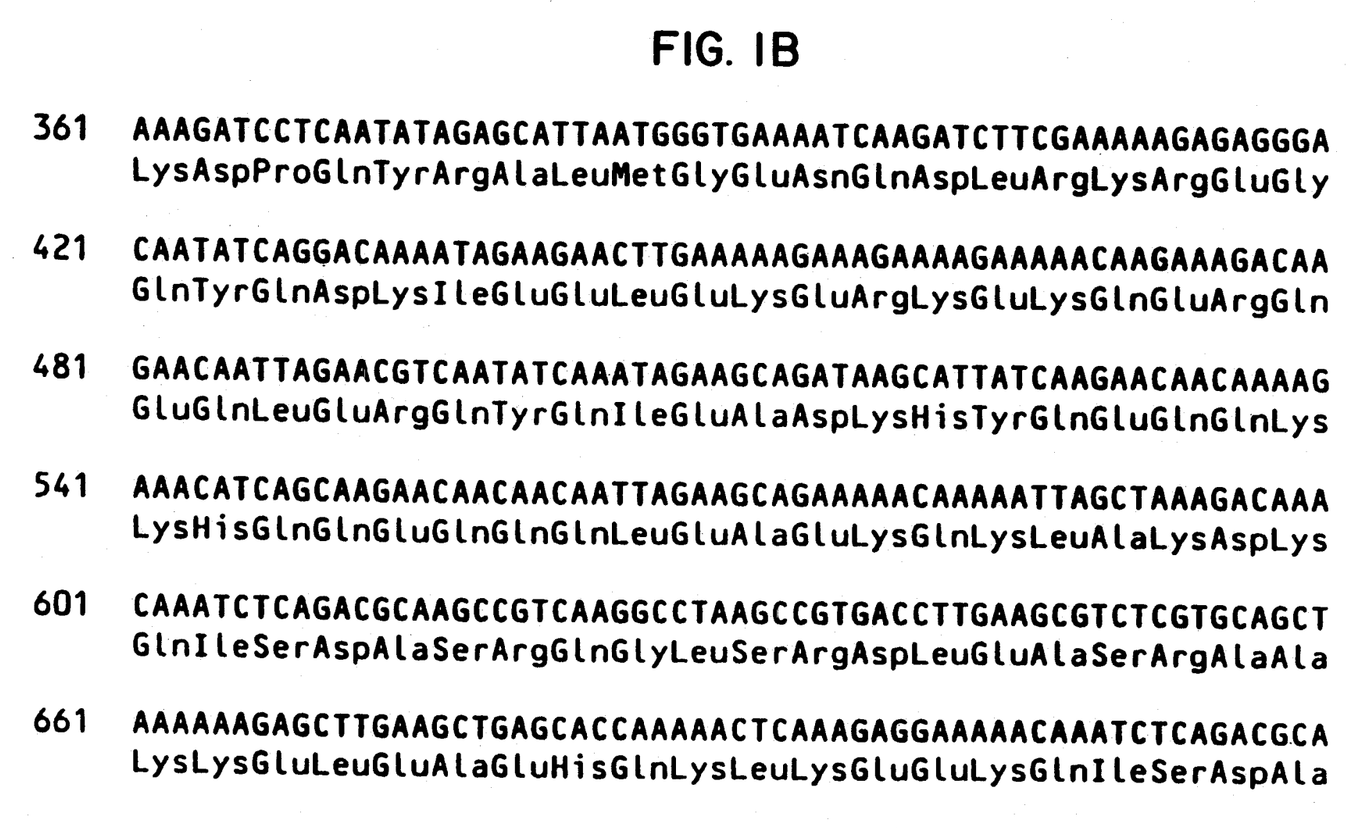
Figure 1C:
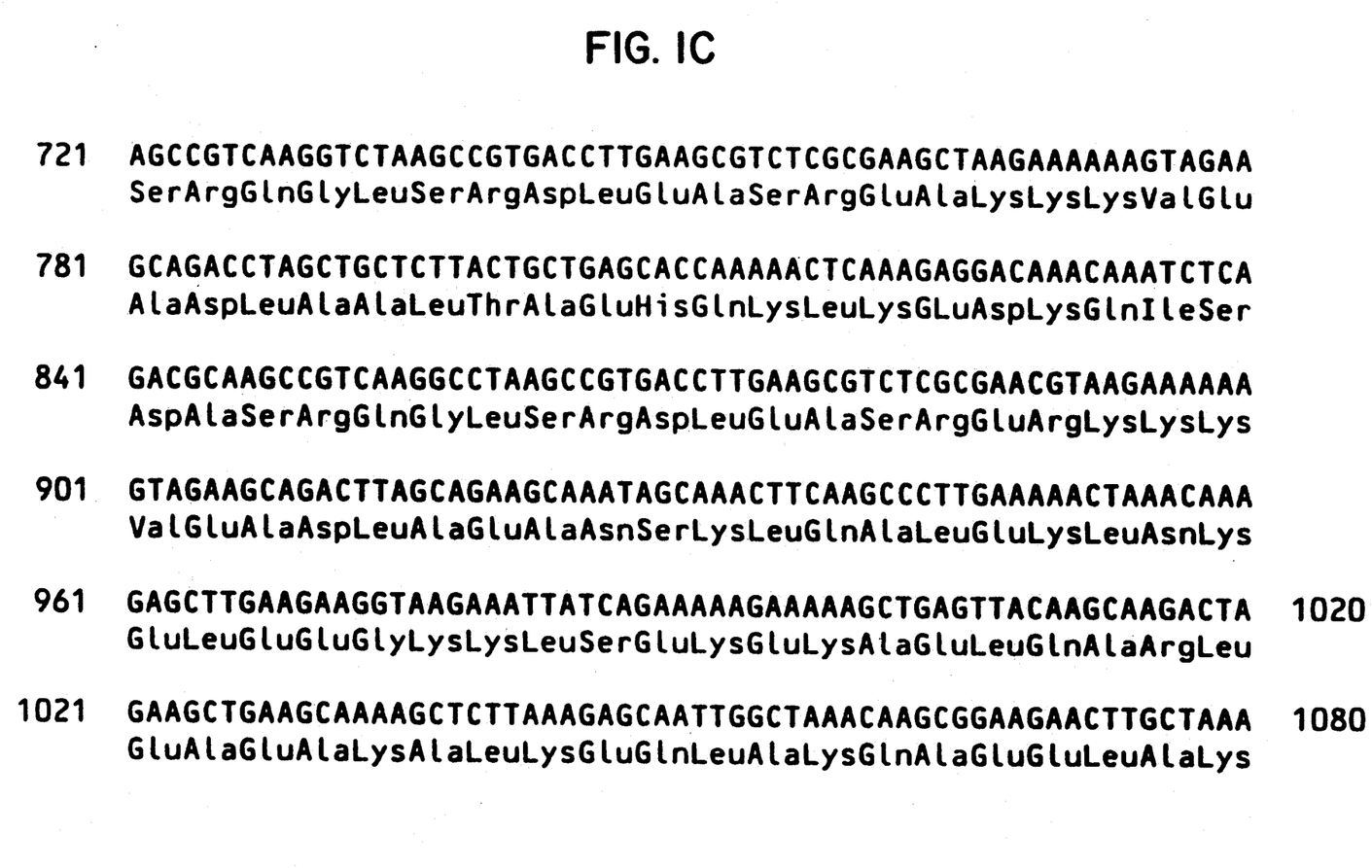
Figure 1D:
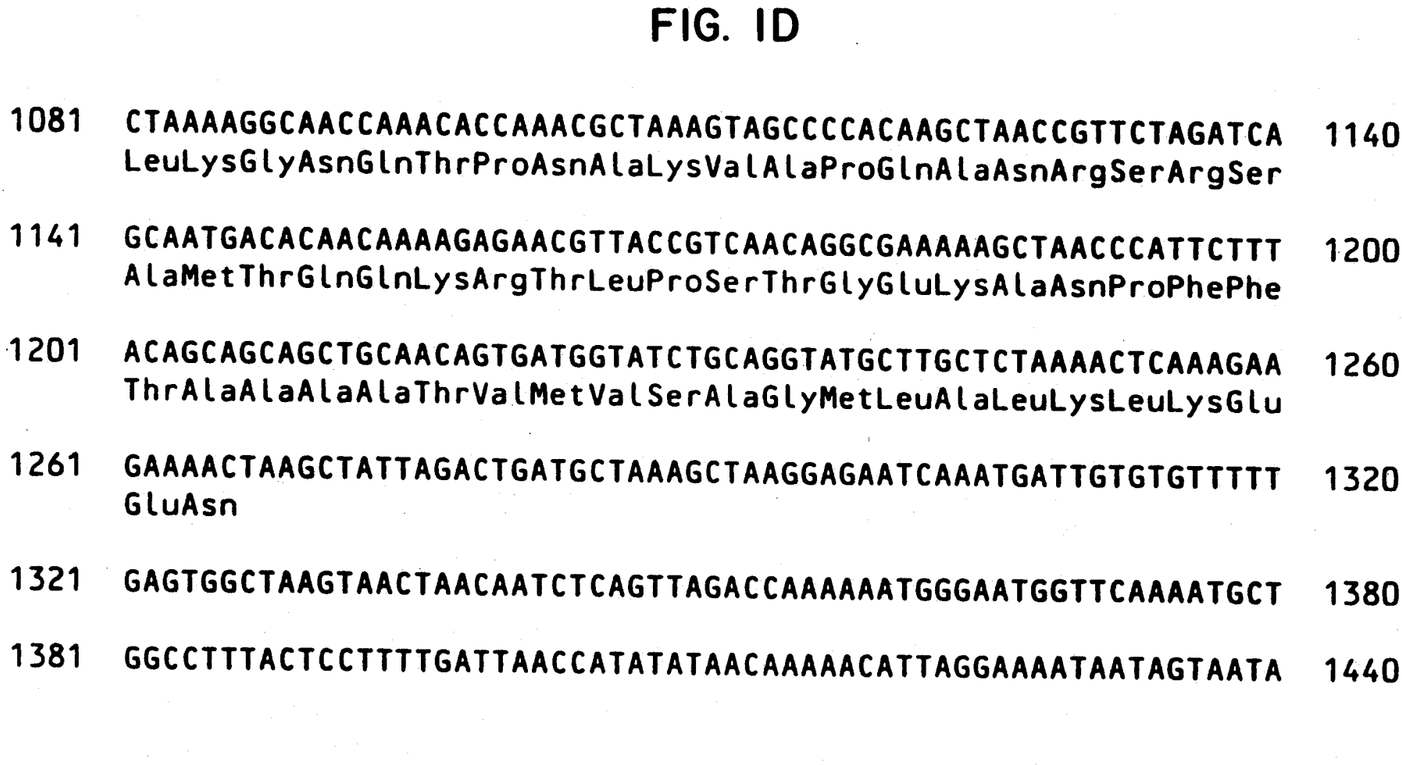
Figure 1E:
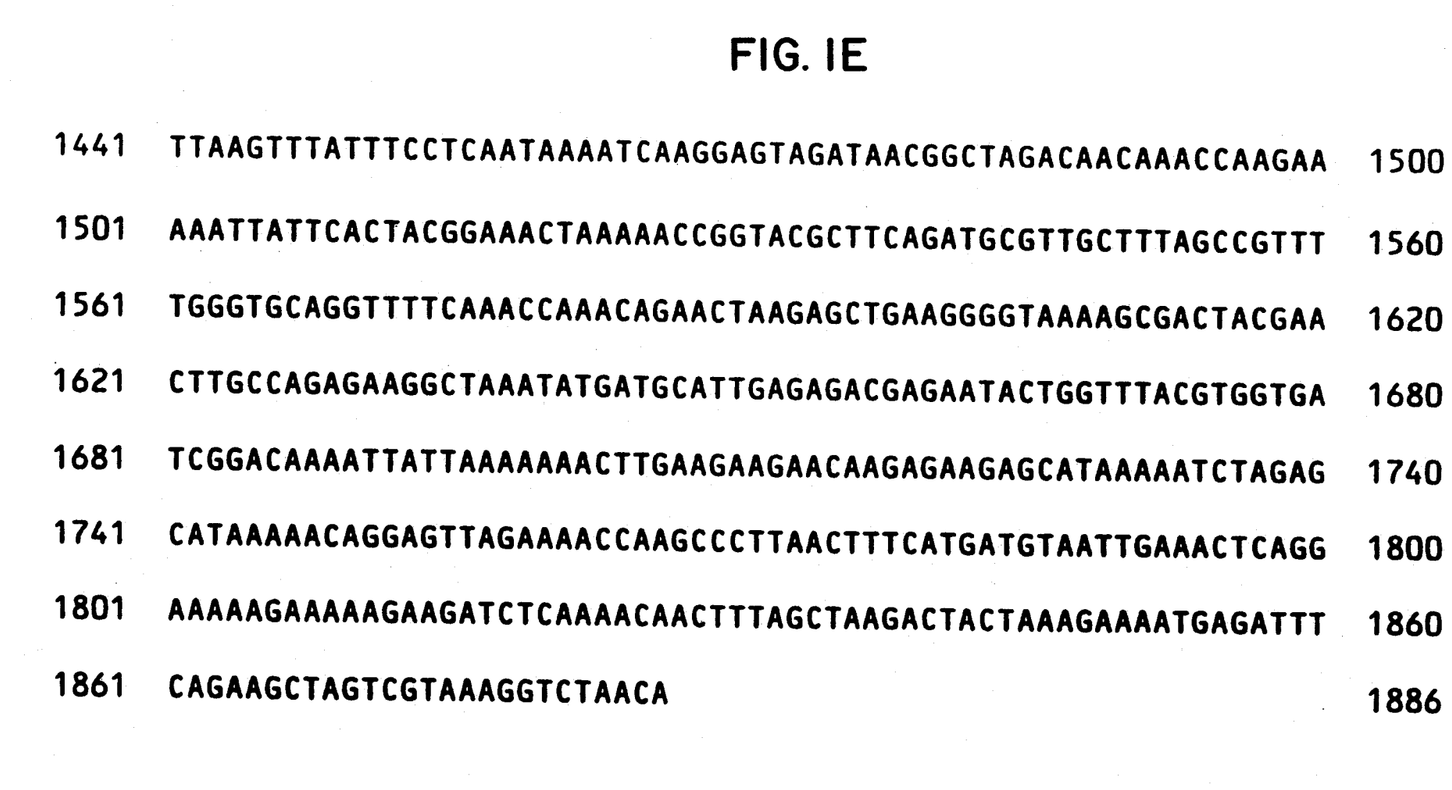
Figure 2:
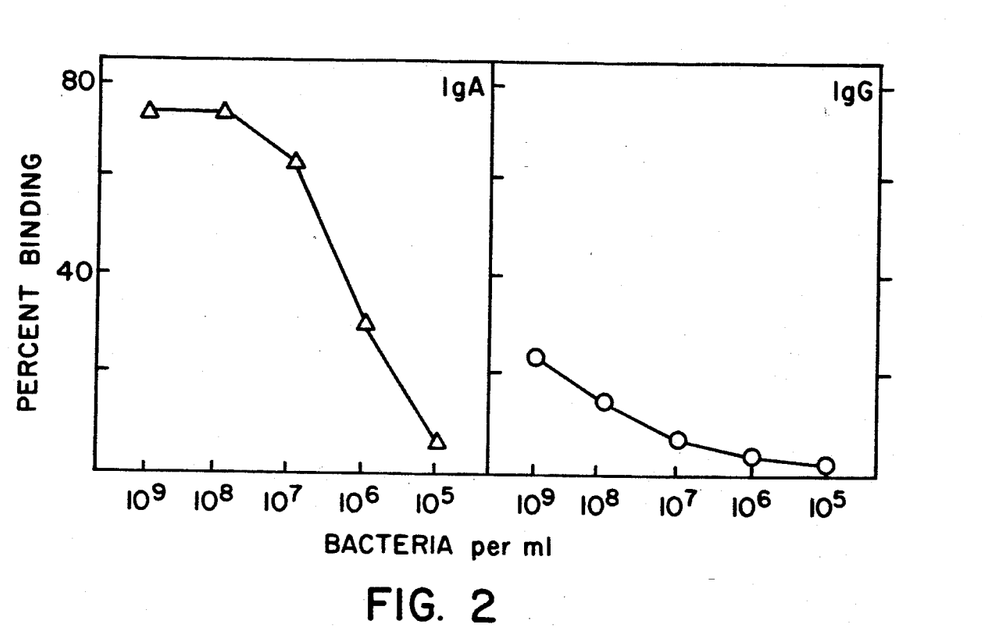
FIG. 2 shows the binding of polyclonal IgA and IgG to Streptococucus strain AP4 at different bacterial concentrations.

After incubation for 60 min, 2 ml of PBSAT were added to each tube and the bacteria were spun down (2000×g for 15 min). The supernatant was discharged and the radioactivity in the pellet was measured in a gamma counter. The quantity bound is expressed in percent of added radioactivity. Non-specific uptake (less than 5%) recorded with the non-binding drain *Staphylococcus epidermidis* L603 has been deduced. In some experiments the ability of a bacterial staring to bind labelled protein was tested at different bacterial concentrations (FIG. 1). In these experiments the test bacteria were diluted n a suspension of non-binding *S. epidermidis* L603 bacteria, to keep the total number of bacteria in the test mixture constant.

Among 104 strains representing a large number of different M types, 23 strains were found to bind more than 50% of added radiolabelled IgA in the standard binding test described above. The capacity of these strains to bind IgA was then compared in experiments where decreasing amounts of bacteria were mixed with a standard amount of labelled IgA (FIG. 1). According to these tests, five of the streptococcal strains had a binding capacity clearly exceeding that of the other strains (data not shown). Two strains were chosen for further study. One of these strains (AW43) belongs to M type 60. The other strain (AP4) belongs to M type 4. The ability of these two strains to bind other immunoglobulins than serum IgA was tested, with very similar results for the two strains (see Table I).

TABLE I

Binding of immunoglobulins to two strains of group A streptococci.

| Immunoglobulin | Binding (%) of added immunoglobulin | |
|---|---|---|
| | strain AW43 | strain AP4 |
| Ig A, serum | 67 | 60 |
| IgA, secretory | 71 | 62 |
| IgA1 | 62 | 49 |
| IgA2 | 45 | 43 |
| IgG | 21 | 20 |
| IgG1 | 16 | 24 |
| IgG2 | 19 | 23 |
| IgG3 | 11 | 20 |
| IgG4 | 23 | 29 |
| IgM | 2 | 1 |

Serum IgA, secretory IgA, IgG and IgM were polyclonal, the other proteins were monoclonal.

Immunoglobulins were of human origin and polyclonal, unless otherwise stated. Serum IgA, secretory IgA and one monoclonal IgA1 protein were from Cooper Biomedical, Malvern. Pa. A second monoclonal IgAI protein was from Calbiochem-Behring, San Diego, Calif. A third monoclonal IgA protein was purified from the serum of a patient with multiple myeloma, using zone electrophoresis in 0.6% agarose, followed by gel filtration. A monoclonal IgA2 protein was the gift of Dr Anders Grubb, Malmö general Hospital; minor amounts of contaminating IgG and albumin were removed by passage through a small column of protein G-Sepharose, which binds both IgG and albumin. IgG was from AB Kabi, Stockholm, Sweden. Monoclonal IgG of all four subclasses was the gift of Dr Lars Björck. IgM was from Calbiochem-Behring. Monoclonal IgD was the gift of Dr Anders Grubb och monoclonal IgE was the gift of Dr Inge Olsson, University of Lund.

Both strains bind secretory IgA and IgA of the two subclasses. In addition, there is a lower degree of binding of IgG (see also FIG. 1). This limited binding of IgG is not due to selective binding of one subclass, since all four subclasses bind equally poorly. There was no significant binding of IgM. The binding of IgA to strain AP4 was further characterized through inhibition tests. Binding of radiolabelled serum IgA could be completely inhibited by the addition of an excess of unlabeled serum IgA or a monoclonal IgA1 protein, but unlabeled IgG did not at all inhibit binding. This result suggests that IgA and IgG bind to separate structures on the surface of this bacterial strain.

The following example is given as an illustration only and is not intended to limitate the invention in any way.

Cloning and expression of the protein Arp gene in *E. coli*

Strain AP4 was chosen for attempts to purify the IgA-binding structure. Preliminary experiments showed that the binding of IgA could be abolished by pretreatment of the bacteria with trypsin, but attempts to demonstrate IgA-binding activity in the solubilized material were unsuccessful. However, these experiments clearly indicated that the binding structure is a protein, which will be called protein Arp 4.

Isolation of DNA from Streptococcus AP4

Streptococcal DNA was isolated essentially as described by Spanier J G and Cleary P P, *Virology*, 130, 514–522 (1983). The method involves preparatory steps in order to make the streptococcal cell wall fragile, which is a prerequisite for efficient lysis. A culture (225 ml) of strain AP4 in Todd-Hewitt broth (Oxoid) (Infusion from 450 g fat-free minced beef grams per liter 10.0, Tryptone 20.0, Dextrose 2.0, Sodium bicarbonate 2.0, Sodium chloride 2.0, Discodium phosphate anhyd. 0.4, pH 7.8±0.2) was grown at 37° C. by shaking to $2 \times 10^8$/ml, when 13 ml of 10% cysteine and 11 ml of 0.4M DL-threonine were added. Incubation was continued for 1 h, followed by the addition of 125 ml 15% glycine.

After 45 min at 37° C. the bacteria centrifused down, washed three times with 0.2M NaAc, and resuspended in 10 ml 0.1M Tris buffer, pH 8.0, containing 25% glucose and 10 mM EDTA. Mutanolysin (Sigma) was added to a concentration of 50 units/ml, followed by incubation at 37° C. for 1 h, when 1.0 ml of 10% SDS (Sodium dodecyl sulphate) was added, causing complete lysis immediately. The lysate was digested with proteinase K (0.1 mg/ml) for 2 h at 37° C., extracted three times with buffer-saturated phenol, and dialyzed against TE buffer (0.01M Tris HC, 1 mM EDTA; pH 7.4). The DNA was purified further by density gradient centrifugation: 1 g of CsCl and 60 µl of ethidium bromide (10 mg/ml) were added per ml of DNA in TE, followed by centrifugation at 45,000 rpm for 24 h at 20° C. in a Beckman VTi 50 rotor. The band containing streptococcal DNA was visualized with ultraviolet light and recovered with a syringe after puncturing of the wall of the tube. The ethidium bromide was removed by extraction with n-butanol saturated with TE, followed by dialysis of the DNA against TE. The yield of DNA was 0.5 mg.

Cloning of the protein Arp 4 gene in lambda EMBL3

Streptococcal DNA was cloned the lambda vector EMBL3 (Genofit SA, Geneva) according to Frischauf, A-M, Lehrach, H, Poustka, A, and Murray, N, *J Mol Biol*, 170, 827–842 (1983). Fifty μg of DNA from strain AP4 in a volume of 100 μl was partially digested with 5 units of Sau 3AI for 1 h at 37° C. Agarose gel electrophoresist showed that a large fraction of this DNA was in the desired size range (10 to 20 kB). The cleaved DNA was ligated to lambda EMBL3 arms and packaged in vitro with Gigapack (Genofit SA, Geneva), as recommenced by the suppliers.

Restriction enzymes and T4 DNA ligase were purchased from New England Biolabs or from Boehringer Mannheim, and were used as recommended by the suppliers.

About $10^5$ p.f.u. were obtained from ligation of 0.25 μg of streptococcal DNA. The library was used without amplification and was plated on the P2 lysogenic host strain *E. coli* P2392 (Genofit SA, Geneva) which only allows lambda phage particles with an insert to form plaques. Plaques were tested for presence of IgA-binding protein with a preroxidase technique: Plates with about 1000 plaques were covered with nitrocellulose filters (Schleicher and Schuell, BA 85) and left at 4° C. for 1 h. The filters were then removed and incubated in VBS (10 mM veronal buffer, 0.15M NaCl, pH 7.4) supplemented with 0.25% gelatin and 0.1% Tween 20, followed by washings for 2×5 min in VBS containing 0.05% Tween 20 ("VBST"). The filters were then incubated of 30 min in VBST containing 10 μl/ml of IgA, followed by washings 2×5 min in VBST. In the following step the filters were incubated for 30 min in VBST containing peroxidase-conjugated rabbit antihuman IgA (Dakopatts, Denmark; 5 μl perm ml of VGST), followed by washings in VBST, 3×5 min. The filters were finally stained for 5 min at pH 5.1 in 50 ml 50 mM acetate buffer containing 25 μl of 30% $H_2O_2$ and 2 ml 1% 3-amino-9-ethyl carbazol in acetone. All incubations were done at room temperature. Plaques containing protein Arp appeared as red spots on the filers. Positive clones wee plaque purified and retested for protein Arp production as described above, ad plate lysates were prepared from verified clones. The frequency of positive clones in the library was approximately 0.05%. Seven positive clones were found and one of these were chosen of further study. The screening method used to detect the positive clone was indirect and it was therefore essential to demonstrate directly that the lambda clone produced an IgA-binding protein. This was done by a spot-test method. A bacterial lawn with spots of the lambda clone was covered with a nitrocellulose filter, allowing adsorption of liberated proteins to the filter. The filter was then analyzed for ability to bind radiolabelled IgA. Spots of the lambda clone with insert from the IgA-binding strain indeed contained material that bound IgA. A lambda control without any insert of streptococcal DNA was completely negative. The lambda clone was called λAP4 IgA # 6.

Nucleotide sequence determination of the insert in λAP4 IgA # 6

Figure 4:
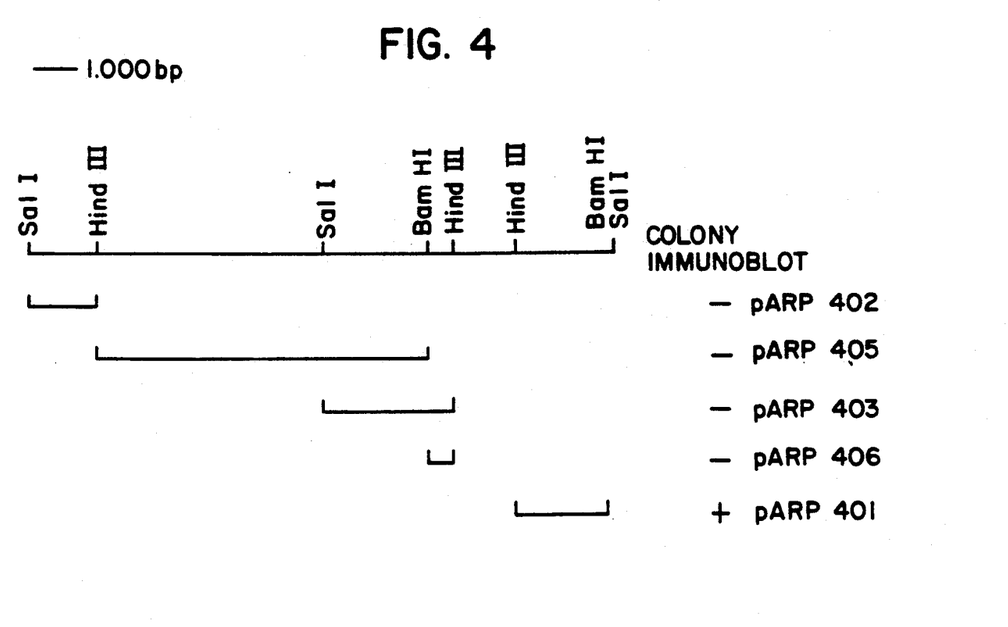
FIG. 4 shows a restriction enzyme fragment map of the insert phage λAp4 IgA # 6.
Figure 5:
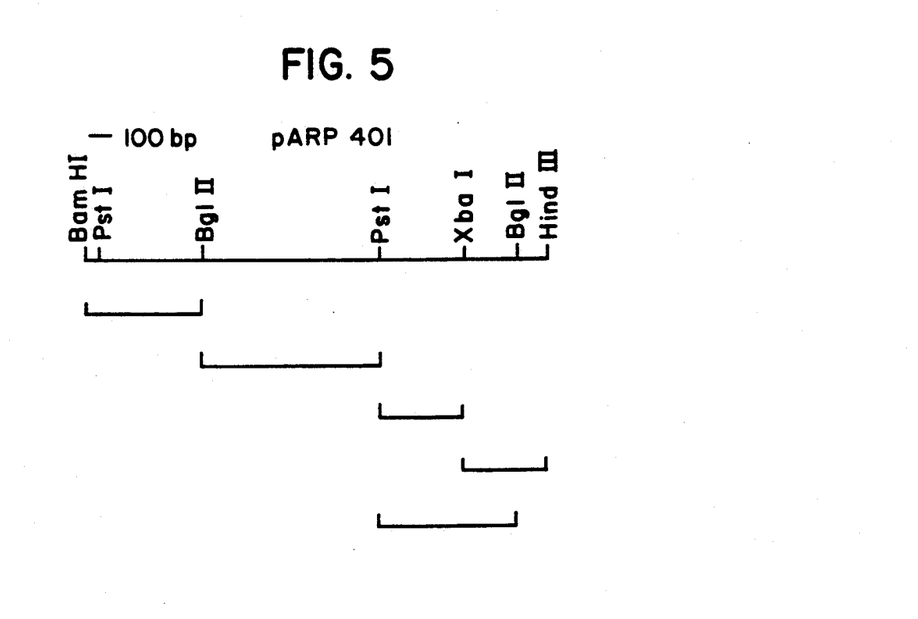
FIG. 5 shows an extended restriction enzyme map of the insert in the plasmid pARP 401.

In order to locate the general for protein Arp 4 in phase λAP4 IgA # 6 a plate stock of the phase was prepared. For each 9 cm petri dish with Luria agar supplemented with glucose, $CaCl_2$, $FeCl_3$, and $MgSO_4$ (Arber, W., Enquist, L., Hohn, B., Muray, N. E., and Murray, K. [1983] in *Lambda II* [Hendrix, R. W., Roberts, J. W., Stahl, F. W., and Weisberg, R. A. eds.]. Cold Spring Harbor, N.Y. Cold Spring Harbor Laboratory) about 50,000 plaque forming units were mixed with about $10^8$ *E. coli* LE392 in 3 ml soft agar which then was poured on the LA plate. The plates were incubated at 37° C. for 8 to 10 hours. The plates were then chilled at +4° C. for 2 hours and 5 ml storage medium (Maniatis, T., Fritsch, E. F., and Sambrook, J. [1982]. *Molecular Cloning: A Laboratory Manual*. Cold Spring Harbor, N.Y. Cold Spring Harbor Laboratory) was added to each plate. After 12–15 hours at +4° C. the liquid was harvested and cells and debri was eliminated by centrifugation. Phases were obtained from 20 plates. The phages were concentrated by polyethylene glycol precipitation as described by Maniatis et al. and after DNase and RNase treatment as described in Maniatis et al. the concentrated phage stock was extracted witch phenol and chloroform as described in Maniatis et al. The extracted DNA was further purified by cesium chloride centrifugation in the presence of ethidium bromide. The DNA was recovered using a syringe and a needle. The ethidium bromide was extracted and the DNA was ethanol precipitated and finally resuspended in 10 mM Tris-HCl, pH 8.0/1 mM EDTA. The DNA was subjected to restriction enzyme analysis using restriction enzymes from Boehringer Mannheim under conditions recommended by the supplier. The DNA fragments were separated on 0.8% agarose gel in Tris-acetate buffer (Maniatis et al.). The restriction enzyme map obtained is presented in FIG. 4. Different DNA fragments were subclones in the plasmid vector pUC18 (Yanisch-OPerron, C., Vierira, J., and Messing, J. [1985], *Gene* 33: 103–119). The ligated material was issued to transform *E.coli* JM83 (Yanisch-Perron et al.) to ampicillin resistance and after 15 minutes exposure to chloroform vapor the bacterial colonies were subject to immunoblot analysis as described above for lambda phases. The results presented in FIG. 4 shows that a 2.2 kilobase pair Hind III-Bam HI fragment is sufficient for expression of protein Arp 4. An extended restriction enzyme map for this fragment is presented in FIG. 5. The nucleotide sequence was determined by cloning different fragments from pARP 401, as indicated in FIG. 5, in the replicative form of the *E. coli* phages M13 mp18 and mp19 (Yanisch-Perron et al.). The ligated material was used to transform *E. coli* JM 103 as described in Messing (Messing, J. [1983], in *Methods in Enzymology* vol. 101 [Wu, R., Grossman, L., and Moldave, K. eds], pp. 20–78). Singel plaques were picked and single stranded DNA was prepared as described by Messing. The nucleotide sequence of the inserts in this phases was determined using the dideoxy chain terminating method of Sanger (Sanger, F., Nicklen, S., and Coulson, A. R. [1977], *Proceedings of the National Academy of Sciences*, USA 74: 5463–5467; and Sanger, F., Coulson, A. R., Barrell, B. G., Smith, A. J. H., and Roe, B. A. [1980], *Journal of Molecular Biology* 143: 161–178) with $^{35}$S dCTP (Amersham) using sequenase $^{IM}$ (Tablr, S. and Richardson, C. C. [1987], *Proceedings of the National Academy of Sciences*, USA 84: 4767–4771) from USB following the protocol provided by the supplier. Autoradiography was done using Fuji X-ray film and intensifying screen. The nucleotide sequence obtained is presented in FIG. 1.

Infection of E. coli with phage λAP4 IgA # 6 containing streptococcal DNA

A large phage lysate (1–2 l) was prepared by infection of a logarithmically growing culture of strain E. coli LE392 at $1 \times 10^8$ bacterial/ml in LB broth (Maniatis et al, 1982, grams per liter: Bactotryptone 10, Bacto-yeast extract 5, NaCl 10; pH 7.5) using the λAP4 IgA # 6-clone. The multiplicity of infection was about $2 \times 10^{-3}$. After lysis the protease inhibitors iodoacetic acid and benzamidinechloride were added to a final concentration of 10 mM and the lysate was centrifuged at 4000 rpm for 1 h at 4° C. The supernatant was used directly for affinity chromatography of frosen and used layer; in the latter case the lysate had to be centrifuged again since new visible debris was formed by the freezing and thawing.

Purification of protein Arp 4 by affinity chromatography

Affinity chromatography was performed with IgA coupled to CNBr-activated Sepharose 4B (Pharmacia, Uppsala, Sweden), 1,3 mg IgA per ml packed gel. 7 ml of IgA-Sepharose was added to the centifuged phase lysate and stirred gently at 4° C. for 6 h. The gel was recovered on a sintered glass filter, washed extensively with PBS (about 2 l) and then transferred to a small column. The column (7 ml) was eluted with 0.1M glycine-HCl, pH 2.0 and fractions (3 ml) were collected. The pH of the fractions was immediately adjusted by the addition of 0.75 ml of 0.5M phosphate buffer, pH 7.4. Fractions were analyzed for protein concentration by absorbance at 280 nm. All measurable protein was recovered in 2 or 3 reactions, which were pooled, dialyzed against PBS and concentrated by centrifugation in a Centricon 10 microconcentrator (Amicon, Danvers, Mass.). The IgA-Sepharose was washed with pbs and stored in PBS + 0.05% azide.

Analysis of molecular weight by electrophoresis and western blotting of proteins Polyacrylamide gel electrophoresis (Bio Rad apparatus) with sodium dodecyl sulphate (SDS-PAGE) was performed in slabs using the buffer system of Laemmli, UK, Nature, 227, 660–684 (1970). The running gelhad a total acrylamide concentration of 10% and the cross-linking was 3.3%. Samples were boiled for 3 min in a solution containing 2% SDS and 5% 2-mercaptoethanol before electrophoresis. A kit from Sigma containing bovine albumin (66 kDa), ovalbumin (45 kDa), glyceraldehyde-3-phosphate (36 kDa), cabonic anhydrase (29 kDa), trypsinogen (24 kDa) and trying inhibitor (20 kDa) was used as markers for mol wt. The separated proteins were stained with Coomassie Brilliant BlueR-250 or transferred to Immobilon membranes by electrophoretic transfer as described by Towbin, H, Staehlin, T and Gordon, J, Proc Nat Acad Sci USA, 76, 4350–4354 (1979), using a Transblot cell from Bio Rad. To saturate free binding sites, the Immobilon membranes were washed $4 \times 20$ min at 40° C. in 250 ml of 10 mM veronal buffer, 0.15M NaCl, pH 7.4 (VBS) containing 0.25% gelatin and 0.25% Tween 20. Membranes were then incubated for 3 h at room temperature in 20 ml of VBS containing 0.1% gelatin and radioactive protein ($2 \times 10^5$ cpm/ml), followed by washings $4 \times 10$ min at room temperature in 250 ml of 1M NaCl, 10 mM EDTA, 0.25% gelatin and 0.25% Tween 20. After air-drying the membranes were autoradiographed at −70° C. using Kodak CEA.C X-ray films and Kodak X-Omat regular intensifying screen.

Figure 3:
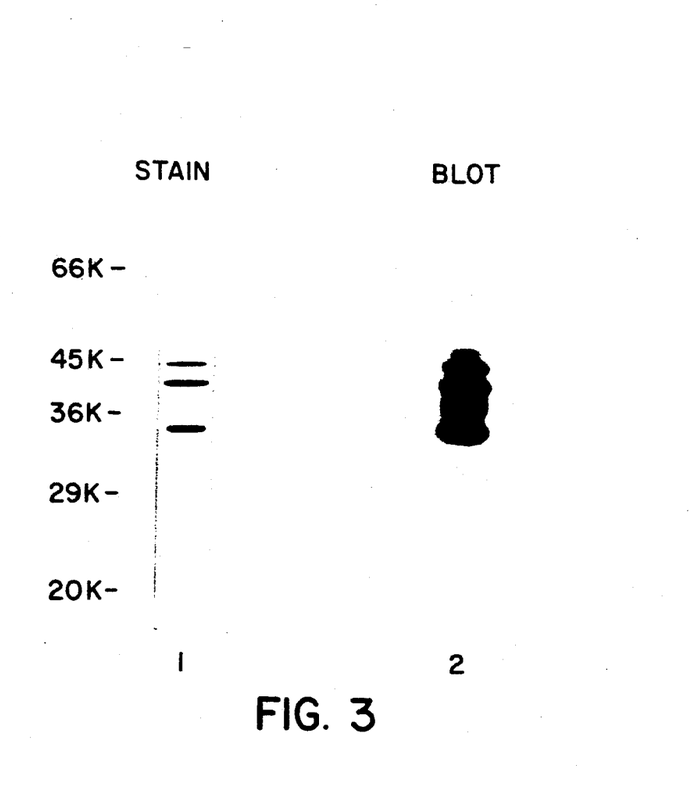
FIG. 3 shows analysis of purified IgA-binding protein (Arp 4) by SDS-polyacrylamide gel electrophoresis. Lanes 1 and 2 show protein Arp 4 purified from a lambda clone expressing IgA binding. Lane 1 was stained with Coomassie brilliant blue; lane 2 was transferred to an Immobilon membrane (Millipore Corp., Bredford, Mass.) and probed with radiolabelled IgA.

The results are shown in FIG. 3. The eluted material was heterogeneous, with major protein bands of 44 kDa, 40 kDa, 34 kDa and minor bands around 37 kDa. These results therefore show that the IgA-Sepharose chromatography allowed complete purification of protein Arp 4 in a single step, an about 10,000-fold purification. The yield of protein Arp 4 was about 0.4 mg from 1 l of phage lysate.

The mol weight pattern seen in FIG. 3 was highly reproducible and seen with several different preparations of protein Arp 4. Furthermore, the same pattern was seen with protein Arp 4 purified from the two independent lambda clones. This strongly indicates that the protein Arp gene was not altered during the cloning procedure.

Detection of IgA bound to Immobilon with radiolabelled protein Arp 4

Radiolabelled protein Arp 4 can be used of detect IgA bound to Immobilon membranes (Millipore) in a dot binding assay, which also demonstrates the specificity of the binding. Serial dilutions of immunoglobulins and some other serum proteins were applied to Immobilon membranes using a dot-blot apparatus from Schliecher and Schuell (Dassel, FRG). The binding specificity of protein Arp 4 was very similar to that of protein Arp 60 (Lindahl and Akerstrom 1988, Molecular Microbiology in press). Thus, there was binding to both serum IgA and secretory IgA as well as to IgA of both subclasses; there was also some binding of IgG, but no binding to IgM, IgD, IgE, albumin, haptoglobin or fibrinogen. The weak binding to polyclonal IgG cannot be due to IgG antibodies to protein Arp 60, since similar results were obtained with monoclonal IgG. A dot-blot experiment also showed that protein Arp 4 binds to both IgA and IgG in the Fc region as previously described for protein Arp 60.

We claim:

1. An Arp4 protein which specifically binds immunoglobulin A and which has the following amino acid sequence beginning with the N-terminus:

AlaGluIle
LysLysProGlnAlaAspSerAlaTrpAsnTrpProLysGluTyrAsnAla

LeuLeuLys

GluAsnGluGluLeuLysValGluArgGluLysTyrLeuSerTyrAlaAsp

AspLysGlu

LysAspProGlnTyrArgAlaLeuMetGlyGluAsnGlnAspLeuArgLys

ArgGluGly

GlnTyrGlnAspLysIleGluGluLeuGluLysGluArgLysGluLysGln

GluArgGln

GluGlnLeuGluArgGlnTyrGlnIleGluAlaAspLysHisTyrGlnGlu

GlnGlnLys

LysHisGlnGlnGluGlnGlnGlnLeuGluAlaGluLysGlnLysLeuAla

LysAspLys

GlnIleSerAspAlaSerArgGlnGlyLeuSerArgAspLeuGluAlaSer

ArgAlaAla

-continued

LysLysGluLeuGluAlaGluHisGlnLysLeuLysGluGluLysGlnIle

SerAspAla

SerArgGlnGlyLeuSerArgAspLeuGluAlaSerArgGluAlaLysLys

LysValGlu

AlaAspLeuAlaAlaLeuThrAlaGluHisGlnLysLeuLysGluAspLys

GlnIleSer

AspAlaSerArgGlnGlyLeuSerArgAspLeuGluAlaSerArgGluArg

LysLysLys

ValGluAlaAspLeuAlaGluAlaAsnSerLysLeuGlnAlaLeuGluLys

LeuAsnLys

GluLeuGluGluGlyLysLysLeuSerGluLysGluLysAlaGluLeuGln

AlaArgLeu

GluAlaGluAlaLysAlaLeuLysGluGlnLeuAlaLysGlnAlaGluGlu

LeuAlaLys

LeuLysGlyAsnGlnThrProAsnAlaLysValAlaProGlnAlaAsnArg

SerArgSer

AlaMetThrGlnGlnLysArgThrLeuProSerThrGlyGluLysAlaAsn

ProPhePhe

ThrAlaAlaAlaAlaThrValMetValSerAlaGlyMetLeuAlaLeuLys

-continued

LeuLysGlu

GluAsn and variants, subfragments or allelic derivates thereof which specifically bind Immunoglobulin A, substantially free of non-immunoglobulin A proteins with which it is naturally associated.

2. A kit for binding, separating and identifying immunoglobulin A comprising said protein or subfragment thereof according to claim 1 and at least one ancillary reagent that facilitates said binding, separation or identification.

3. A composition comprising said protein or subfragment thereof according to claim 1 in an amount sufficient to effect absorption of immunoglobulin A, together with a carrier or support.

4. A protein (called Arp) with apparent molecular weight of about 42 kDa (on sodium dodecylsulpate-polyacrylamide gel electrophoresis) which specifically binds immunoglobulin A, and subfragments thereof which specifically bind immunoglobulin A, substantially free of non-immunoglobulin A proteins with which it is naturally associated.

5. A kit for binding, separating and identifying immunoglobulin A comprising said protein or subfragment thereof according to claim 4 and at least one ancillary reagent that facilitates said binding, separation or identification.

6. A composition comprising said protein or subfragment thereof according to claim 4 in an amount sufficient to effect absorption of immunoglobulin A, together with a carrier or support.

* * * * *